United States Patent [19]

Horton, Jr. et al.

[11] Patent Number: 6,080,266

[45] Date of Patent: Jun. 27, 2000

[54] FRACTIONATION PROCESS FOR CELLULOSIC FIBERS

[75] Inventors: James Ellis Horton, Jr., Appleton; Kristin Ann Goerg-Wood, Sherwood; Jacek Dutkiewicz; Sheng-Hsin Hu, both of Appleton, all of Wis.

[73] Assignee: Kimberly-Clark Worldwide, Inc., Neenah, Wis.

[21] Appl. No.: 09/411,018

[22] Filed: Oct. 1, 1999

Related U.S. Application Data

[63] Continuation of application No. 08/767,612, Dec. 17, 1996.
[51] Int. Cl.⁷ .............................. B32B 31/00; A61F 13/15
[52] U.S. Cl. ...................... 156/300; 156/301; 156/308.2; 162/55; 162/109; 442/334; 604/378
[58] Field of Search ............................. 162/55, 100, 141, 162/149, 111, 109; 604/358, 374, 378, 367; 428/393, 398, 153, 154, 218, 212; 442/334, 352; 156/300, 301, 308.2

[56] References Cited

U.S. PATENT DOCUMENTS

| | | | |
|---|---|---|---|
| 3,085,927 | 4/1963 | Pesch | 162/55 |
| 3,340,138 | 9/1967 | Braun et al. | 162/28 |
| 4,710,187 | 12/1987 | Boland et al. | 604/385 A |
| 4,762,521 | 8/1988 | Roessler et al. | 604/38 SA |
| 4,770,656 | 9/1988 | Proxmire et al. | 604/393 |
| 4,798,603 | 1/1989 | Meyer et al. | 604/378 |
| 5,405,499 | 4/1995 | Vinson | 162/100 |
| 5,503,710 | 4/1996 | Horng | 162/6 |
| 5,582,685 | 12/1996 | Vinson | 162/55 |
| 5,843,852 | 12/1998 | Dutkiewicz et al. | 442/334 |
| 5,849,405 | 12/1998 | Wang et al. | 428/304.4 |
| 5,972,487 | 10/1999 | Duenk et al. | 428/218 |
| 6,015,935 | 1/2000 | LaVon et al. | 604/378 |

FOREIGN PATENT DOCUMENTS

| | | |
|---|---|---|
| 0 094 842 A1 | 11/1983 | European Pat. Off. . |
| 0 540 041 A1 | 5/1993 | European Pat. Off. . |
| WO 96/04424 A1 | 2/1996 | WIPO . |
| WO 97/23184 A1 | 7/1997 | WIPO . |

OTHER PUBLICATIONS

TAPPI Classical Test Method T233 cm–95, "Fiber Length Of Pulp By Classification," published by the TAPPI Press, Atlanta, Georgia, revised 1995, pp. 1–6.

Kibblewhite, R. P., "Effect Of Beating On Fibre Morphology And Fibre Surface Structure," Appita, vol. 26, No. 3, Nov. 1972, pp. 196–202.

Smith, William E. and Von L. Byrd, "Fiber Bonding And Tensile Stress–Strain Properties Of Earlywood And Latewood Handsheets," USDA, Forest Service, Research Paper, FPL 193, 1972, pp. 1–8.

Watson, A. J. and H. E. Dadswell, "Influence Of Fibre Morphology On Paper Properties: Part II. Early Wood And Late Wood," Appita, vol. 15, No. 6, May 1962, pp. 116–128.

Jones, E. D., R. T. Campbell, and G. G. Nelson, Jr., "Springwood–Summerwood Separation Of Southern Pine Pulp To Improve Paper Qualities," Tappi, vol. 49, No. 9, Sep. 1966, pp. 410–414.

Primary Examiner—Stanley S. Silverman
Assistant Examiner—José A. Fortuna
Attorney, Agent, or Firm—Sebastian C. Pugliese, III

[57] ABSTRACT

Disclosed is a process for fractionating cellulosic fibers that is effective to result in cellulosic fibers that exhibit desired properties such as fiber length and fiber coarseness values. The fractionating process is quite efficient and has been found to produce cellulosic fibers that are more homogeneous in their properties as compared to the starting mixture of cellulosic fibers. Also disclosed is a handsheet prepared from the fractionated cellulosic fibers for use in disposable absorbent products.

19 Claims, No Drawings

FRACTIONATION PROCESS FOR CELLULOSIC FIBERS

This application is a continuation of application Ser. No. 08/767,612 entitled "Fractionation Process for Cellulosic Fibers" and filed in the U.S. Patent and Trademark Office on Dec. 17, 1996. The entirety of application Ser. No. 08/767,612 is hereby incorporated by reference.

BACKGROUND OF THE INVENTION

1. Field of the Invention

The present invention relates to a process for fractionating cellulosic fibers. The cellulosic fibers prepared from such a process may be used to prepare a handsheet or other structure that may be used in a disposable absorbent product intended for the absorption of fluids such as body fluids. Other possible applications of these fibers include various disposable paper products such as tissue and towel.

2. Description of the Related Art

Cellulosic fibers are well known and are used in a wide variety of applications. However, natural or generally untreated cellulosic fibers have been found to generally not provide a level of performance that is desired in certain applications such as the absorption or handling of fluids such as body fluids. As such, it is often desirable to increase the liquid absorbent capacity or the resiliency of the cellulosic fibers being used in such applications. Typically, this has meant that the cellulosic fibers being used have been structurally modified in order to improve the performance of such modified fibers in a particular application.

One known method for modifying cellulosic fibers is to chemically crosslink the cellulosic fibers. In general, a chemical crosslinking agent is added to either a solution containing cellulosic fibers or to swollen cellulosic fibers. The chemical crosslinking agent is then allowed to form crosslinks either within an individual cellulosic fiber or between separate cellulosic fibers. Such processes inherently result in the use of a separate crosslinking agent thereby increasing the costs of manufacturing the chemically crosslinked cellulosic fibers. Additionally, the use of certain crosslinking agents typically requires specialized handling procedures, further increasing the costs of manufacturing, and potentially limiting the applications for which the chemically crosslinked cellulosic fibers may be used. Another disadvantage concerning the use of chemical crosslinking agents is that they are often based on chemicals such as aldehydes which exhibit certain degrees of toxicity.

A variety of chemical treatments of cellulosic fibers are also known. An example of a well known chemical treatment of cellulosic fibers is a mercerization process wherein cellulosic fibers are treated with, typically, sodium hydroxide under suitable conditions to convert the cellulose from its native form into a more thermodynamically stable, less crystalline form. Because the mercerized cellulose is less crystalline and more amorphous, the mercerized cellulose is generally more accessible for further treatment with additional reagents.

These and other known processes for chemically treating cellulosic fibers typically disperse the cellulosic fibers in a solvent, such as an aqueous solution. However, it has been generally recognized that in order to ensure proper mixing of the cellulosic fibers and whatever chemicals are being used to treat the cellulosic fibers as well as to ease the bulk transport of the treatment mixture, such known processes must have the cellulosic fibers present in the solvent at a low consistency. Such processes therefore generally result in the use of more of the solvent in which the chemical treatment takes place, or the chemical treatment agent being used, than would ideally be needed, thereby increasing the costs of manufacturing the chemically treated cellulosic fibers. Additionally, the use of sodium hydroxide, or other caustic agents, typically requires specialized handling procedures as well as recycling processes to ensure that such materials are not discharged to the environment.

Another known method for modifying cellulosic fibers is to mechanically treat the cellulosic fibers. One example of such a mechanical treatment process is wherein the cellulosic fibers are subjected to a high shear force which generally results in highly twisted or curled cellulosic fibers. However, such mechanical treatment processes generally require the use of specialized equipment and the use of large amounts of energy, thereby increasing the costs of manufacturing the mechanically treated cellulosic fibers. Besides, without any additional treatment, the fibers modified only by mechanical treatment generally do not preserve their curl in wet conditions because they swell and collapse. Therefore, mechanical modification is generally not quite sufficient for cellulosic fibers which are used for absorbent structures requiring more porosity or capacity.

It is therefore an object of the present invention to provide a process for the preparation of cellulosic fibers in which the amount of solvent and chemical treatment agents used in the process is minimized or completely eliminated.

It is also an object of the present invention to provide a process for the preparation of cellulosic fibers which will significantly reduce the costs of manufacturing.

It is also an object of the present invention to prepare fractionated cellulosic fibers that exhibit improved liquid handling properties as compared to unfractionated cellulosic fibers.

It is also an object of the present invention to prepare fractionated cellulosic fibers that are useful in preparing paper filter structures.

SUMMARY OF THE INVENTION

The present invention concerns an efficient and effective manner for fractionating cellulosic fibers as well as the fractionated cellulosic fibers prepared from such a process.

One aspect of the present invention concerns a process for fractionating cellulosic fibers wherein the cellulosic fibers are subjected to a fractionating means that is effective to result in fractionated cellulosic fibers that exhibit desired properties.

One embodiment of such a process for fractionating cellulosic fibers comprises subjecting a first cellulosic fiber mixture to a fractionating means effective to separate the first cellulosic fiber mixture into a second cellulosic fiber mixture and a third cellulosic fiber mixture, wherein the second cellulosic fiber mixture exhibits a Fiber Coarseness value that is greater than about 20 milligrams per 100 meters and a Population Average Fiber Length value that is greater than about 0.9 millimeters.

In another aspect, the present invention concerns the fractionated cellulosic fibers prepared by the process disclosed herein.

One embodiment of such an aspect of the present invention is a fractionated cellulosic fiber mixture wherein said fractionated cellulosic fiber mixture exhibits a Fiber Coarseness value that is greater than about 20 milligrams per 100 meters and a Population Average Fiber Length value that is greater than about 0.9 millimeters, wherein the cellulosic fiber mixture is prepared by a fractionation process.

In another aspect, the present invention concerns an absorbent structure comprising fractionated cellulosic fibers prepared by the process disclosed herein.

One embodiment of such an absorbent structure is a handsheet comprising the fractionated cellulosic fibers prepared by the process disclosed herein, wherein the handsheet is prepared by a wet-laid process.

DETAILED DESCRIPTION OF THE PREFERRED EMBODIMENTS

It has been discovered that, by using a fractionation process for separating an initial cellulosic fiber mixture into different, distinct cellulosic fiber mixtures, fractionated cellulosic fibers exhibiting desired properties may be prepared by an efficient and effective process.

As used herein, the term "fractionation" is meant generally to refer to the separation of a mixture into separate components and, more particularly, to the separation of a cellulosic fiber mixture into separate cellulosic fiber fractions.

A wide variety of cellulosic fibers can be employed in the process of the present invention. Illustrative cellulosic fibers include, but are not limited to, wood and wood products, such as wood pulp fibers; non-woody paper-making fibers from cotton, from straws and grasses, such as rice and esparto, from canes and reeds, such as bagasse, from bamboos, form stalks with bast fibers, such as jute, flax, kenaf, cannabis, linen and ramie, and from leaf fibers, such as abaca and sisal. It is also possible to use mixtures of one or more cellulosic fibers. Suitably, the cellulosic fiber used is from a wood source. Suitable wood sources include softwood sources such as pines, spruces, and firs, and hardwood sources such as oaks, eucalyptuses, poplars, beeches, and aspens.

As used herein, the term "fiber" or "fibrous" is meant to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less.

It is generally desired that the cellulosic fibers used herein be wettable. As used herein, the term "wettable" is meant to refer to a fiber or material which exhibits a water in air contact angle of less than 90°. Suitably, the cellulosic fibers useful in the present invention exhibit a water in air contact angle between about 10° to about 50° and more suitably between about 20° to about 30°. Suitably, a wettable fiber refers to a fiber which exhibits a water in air contact angle of less than 90°, at a temperature between about 0° C. and about 100° C., and suitably at ambient conditions, such as about 23° C.

Suitable cellulosic fibers are those which are naturally wettable. However, naturally nonwettable fibers can also be used. It is possible to treat the fiber surfaces by an appropriate method to render them more or less wettable. When surface treated fibers are employed, the surface treatment is desirably nonfugitive; that is, the surface treatment desirably does not wash off the surface of the fiber with the first liquid insult or contact. For the purposes of this application, a surface treatment on a generally nonwettable fiber will be considered to be nonfugitive when a majority of the fibers demonstrate a water in air contact angle of less than 90° for three consecutive contact angle measurements, with drying between each measurement. That is, the same fiber is subjected to three separate contact angle determinations and, if all three of the contact angle determinations indicate a contact angle of water in air of less than 90°, the surface treatment on the fiber will be considered to be nonfugitive. If the surface treatment is fugitive, the surface treatment will tend to wash off of the fiber during the first contact angle measurement, thus exposing the nonwettable surface of the underlying fiber, and will demonstrate subsequent contact angle measurements greater than 90°. Beneficial wettability agents include polyalkylene glycols, such as polyethylene glycols. The wettability agent is used in an amount comprising beneficially less than about 5 weight percent, suitably less than about 3 weight percent, and more suitably less than about 2 weight percent, of the total weight of the fiber, material, or absorbent structure being treated.

In the present invention, it is desired that the cellulosic fibers be used in a form wherein the cellulosic fibers have already been prepared into a pulp. As such, the cellulosic fibers will be substantially in the form of individual cellulosic fibers, although such individual cellulosic fibers may be in an aggregate form such as a pulp sheet, in contrast with untreated cellulosic forms such as wood chips or the like. Thus, the current process is generally a post-pulping, cellulosic fiber separation process as compared to other processes that are generally used for high-yield pulp manufacturing processes.

The obtaining or preparation of cellulosic fibers from most cellulosic sources typically results in a heterogeneous mixture of cellulosic fibers wherein the individual cellulosic fibers in the mixture exhibit a broad spectrum of values for a variety of properties such as length, coarseness, diameter, curl, color, chemical modification, cell wall thickness, fiber flexibility, and hemicellulose and/or lignin content. As such, seemingly similar mixtures of cellulosic fibers prepared from the same cellulosic source may exhibit different mixture properties, such as freeness, water retention, and fines content because of the difference in actual cellulosic fiber make-up of each mixture. Also, depending on the application for which the cellulosic fibers are intended, a fraction of the cellulosic fibers in a particular mixture may be appropriate for such intended use whereas the rest of the cellulosic fibers in the particular mixture may not be appropriate for such intended use.

In the present invention, it has been discovered that the use of a fractionation process alone can be sufficient to effectively obtain cellulosic fibers such that the fractionated cellulosic fibers exhibit desired properties, particularly desired liquid absorbency properties.

In the present invention, a fractionation means is used to separate a cellulosic fiber mixture into distinct components. Fractionation means that are suitable for use in the present invention include, but are not limited to, typical equipment used to separate contaminants and/or inks from cellulosic fibers such as low-consistency washers, intermediate-consistency washers, high-consistency washers, flotation cells, flotation machines, centrifugal cleaners, pressure screens, and gravity screens. Such separation equipment is well known and is described in various pulp and paper journals and text books.

Generally, such fractionation should be done under conditions such that the cellulosic fibers being fractionated are not damaged such as by degradation or by undesirable physical modification. Otherwise, however, the conditions under which a cellulosic fiber mixture is fractionated are not critical and may include a wide range of temperatures, pressures, consistencies, humidities and other conditions.

In one embodiment of the present invention, the process for fractionating cellulosic fibers comprises subjecting a first cellulosic fiber mixture to a fractionating means effective to separate the first cellulosic fiber mixture into a second cellulosic fiber mixture and a third cellulosic fiber mixture, wherein the second cellulosic fiber mixture exhibits desired properties.

In general, the cellulosic fibers may be used in the process of the present invention in either a dry or a wet state. However, it may be desirable to prepare an aqueous mixture comprising the cellulosic fibers wherein the aqueous mixture is agitated, stirred, or blended to effectively disperse the cellulosic fibers throughout the water. In one embodiment of the present invention, it is desired that the cellulosic fibers be fractionated when the cellulosic fibers are in the form of aqueous pulp mixture that beneficially has a consistency of between greater than about 0 to about 100 weight percent, suitably between greater than about 0 to about 20 weight percent, and more suitably between greater than about 0 to about 5 weight percent cellulosic fibers, based on the total weight percent of the aqueous pulp mixture.

As used herein, "consistency" is meant to refer to the concentration of the cellulosic fibers present in an aqueous mixture. As such, the consistency will be presented as a weight percent representing the weight amount of the cellulosic fibers present in an aqueous mixture divided by the total weight amount of cellulosic fibers and water present in such mixture, multiplied by 100.

The cellulosic fibers are typically mixed with an aqueous solution wherein the aqueous solution beneficially comprises at least about 30 weight percent water, suitably about 50 weight percent water, more suitably about 75 weight percent water, and most suitably 100 weight percent water. When another liquid is employed with the water, such other suitable liquids include methanol, ethanol, isopropanol, and acetone. However, the use or presence of such other non-aqueous liquids may impede the formation of an essentially homogeneous mixture such that the cellulosic fibers do not effectively disperse into the aqueous solution and effectively or uniformly mix with the water. Such a mixture should generally be prepared under conditions that are sufficient for the cellulosic fibers and water to be effectively mixed together. Generally, such conditions will include using a temperature that is between about 10° C. to about 100° C.

In general, cellulosic fibers are prepared by pulping or other preparation processes in which the cellulosic fibers are present in an aqueous solution. For use in certain fractionation processes of the present invention, therefore, it may be possible to use an aqueous solution directly from such preparation processes without having to separately recover the cellulosic fibers.

Specific fractions of a cellulosic fiber mixture have been discovered to exhibit improved properties that make such fractionated cellulosic fibers suitable for use in liquid absorption or liquid handling applications.

In one embodiment of the present invention, it is desired that a specific fraction of a cellulosic fiber mixture exhibit a desired fiber length such as a population average fiber length. As used herein, "population average fiber length" is meant to represent the sum of all of the lengths of the fibers in a fiber sample divided by the number of fibers in the fiber sample. It has been discovered that if the population average fiber length value for a cellulosic fiber mixture is too low, absorbent structures prepared from such a cellulosic fiber mixture will generally not exhibit desired liquid absorbent or transport properties. It has also been discovered that if the population average fiber length value for a cellulosic fiber mixture is too high, absorbent structures prepared from such a cellulosic fiber mixture will generally not exhibit desired liquid absorbent or transport properties. As such, it is generally desired that a recovered fraction of cellulosic fibers exhibit a Population Average Fiber Length value that is beneficially at least about 0.9 millimeter, more beneficially at least about 1.0 millimeter, suitably at least about 1.1 millimeter, more suitably at least about 1.25 millimeter, most suitably at least about 1.5 millimeter, and up to about 50 millimeters. The Population Average Fiber Length value for a cellulosic fiber mixture or fraction may be determined according to the procedure described in the Test Methods section herein.

In one embodiment of the present invention, it is desired that a specific fraction of a cellulosic fiber mixture exhibit a desired coarseness. As used herein, "coarseness" is meant to represent the weight of the fibers per unit length of the fibers, such as milligrams of fiber per 100 meters of fiber length. It has been discovered that if the coarseness value for a cellulosic fiber mixture is too low, absorbent structures prepared from such a cellulosic fiber mixture will generally not exhibit desired liquid absorbent or transport properties. It has also been discovered that if the coarseness value for a cellulosic fiber mixture is too high, absorbent structures prepared from such a cellulosic fiber mixture will generally not exhibit desired liquid absorbent or transport properties. As such, it is generally desired that a recovered fraction of cellulosic fibers exhibit a Coarseness value that is beneficially at least about 20, more beneficially at least about 22, suitably at least about 24, more suitably at least about 26, most suitably at least about 30, and up to about 100 grams per 100 meters. The Coarseness value for a cellulosic fiber mixture or fraction may be determined according to the procedure described in the Test Methods section herein.

After the cellulosic fibers have been effectively fractionated, the specific fractions of the cellulosic fibers are suitable for use in a wide variety of applications. However, depending on the use intended for the fractionated cellulosic fibers, such fractionated cellulosic fibers may be washed with water. If any additional processing procedures are planned because of the specific use for which the treated cellulosic fibers are intended, other recovery and post-treatment steps are also well known.

The cellulosic fibers fractionated according to the process of the present invention are suited for use in disposable absorbent products such as diapers, adult incontinent products, and bed pads; in catamenial devices such as sanitary napkins, and tampons; other absorbent products such as wipes, bibs, wound dressings, and surgical capes or drapes; and tissue-based products such as facial or bathroom tissues, household towels, wipes and related products. Accordingly, in another aspect, the present invention relates to a disposable absorbent product comprising the cellulosic fibers fractionated according to the process of the present invention.

In one embodiment of the present invention, the fractionated fibers prepared according to the process of the present invention are formed into a handsheet which might represent a tissue-based product. Such a handsheet may be formed by either a wet-laid or an air-laid process. A wet-laid handsheet may be prepared according to the method disclosed in the Test Methods section herein.

It has been discovered that a wet-laid handsheet prepared from the fractionated cellulosic fibers prepared according to the process of the present invention may exhibit a density that is lower than a wet-laid handsheet prepared from cellulosic fibers that have not been fractionated according to the process of the present invention.

It has also been discovered that a wet-laid handsheet prepared from the fractionated cellulosic fibers obtained according to the process of the present invention may exhibit a liquid wicking time that is faster than a wet-laid handsheet prepared from cellulosic fibers that have not been fractionated according to the process of the present invention.

It has also been discovered that a wet-laid handsheet prepared from the fractionated cellulosic fibers prepared according to the process of the present invention may exhibit a liquid wicking flux that is higher than a wet-laid handsheet prepared from cellulosic fibers that have not been fractionated according to the process of the present invention.

It has also been discovered that a wet-laid handsheet prepared from the fractionated cellulosic fibers prepared according to the process of the present invention may exhibit an increased bulk and higher absorbent capacity than a wet-laid handsheet prepared from cellulosic fibers that have not been fractionated according to the process of the present invention.

In one embodiment of the present invention, the fractionated cellulosic fibers prepared according to the process of the present invention are formed into a fibrous matrix for incorporation into an absorbent structure. A fibrous matrix may take the form of, for example, a batt of comminuted wood pulp fluff, a tissue layer, a hydroentangled pulp sheet, or a mechanically softened pulp sheet. An exemplary absorbent structure is generally described in copending U.S. patent application, Ser. No. 60/008,994, by Jacek Dutkiewicz, filed Dec. 21, 1995, which reference is incorporated herein in its entirety by reference.

A fibrous matrix useful in the present invention may be formed by an air-laying process or a wet-laid process, or by essentially any other process known to those skilled in the art for forming a fibrous matrix.

In one embodiment of the present invention, a disposable absorbent product is provided, which disposable absorbent product comprises a liquid-permeable topsheet, a backsheet attached to the liquid-permeable topsheet, and an absorbent structure positioned between the liquid-permeable topsheet and the backsheet, wherein the absorbent structure comprises fractionated cellulosic fibers prepared using the process of the present invention.

Exemplary disposable absorbent products are generally described in U.S. Pat. No. 4,710,187; U.S. Pat. No. 4,762, 521; U.S. Pat. No. 4,770,656; and U.S. Pat. No. 4,798,603; which references are incorporated herein by reference.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films.

Absorbent products and structures according to all aspects of the present invention are generally subjected, during use, to multiple insults of a body liquid. Accordingly, the absorbent products and structures are desirably capable of absorbing multiple insults of body liquids in quantities to which the absorbent products and structures will be exposed during use. The insults are generally separated from one another by a period of time.

One liquid transport property desired of the absorbent structure of the present invention is that the absorbent structure exhibits a Vertical Liquid Flux rate, at a height of about 15 centimeters, suitably of at least about 0.002 grams of liquid per minute per gram per square meter of absorbent structure (gsm) per inch of cross-sectional width of the absorbent structure (g/(min*gsm*inch), more suitably of at least about 0.0025 g/(min*gsm*inch), most suitably of at least about 0.003 g/(min*gsm*inch), and up to about 0.1 g/(min*gsm*inch). As used herein, the Vertical Liquid Flux rate value of an absorbent structure is meant to represent the amount of liquid transported across a boundary a specified vertical distance away from a centralized liquid insult location per minute per normalized quantity of the absorbent structure. The Vertical Liquid Flux rate, at a height of about 15 centimeters, of an absorbent structure may be measured according to the test method described herein.

Another liquid transport property desired of the absorbent structure of the present invention is that the absorbent structure exhibits a Vertical Liquid Flux rate, at a height of about 5 centimeters, suitably of at least about 0.01 g/(min*gsm*inch), more suitably of at least about 0.015 g/(min*gsm*inch), most suitably of at least about 0.02 g/(min*gsm*inch), and up to about 0.5 g/(min*gsm*inch). The Vertical Liquid Flux rate, at a height of about 5 centimeters, of an absorbent structure may be measured according to the test method described herein.

Another liquid transport property desired of the absorbent structure of the present invention is that the absorbent structure exhibits a Wicking Time value of a liquid to an elevation of 15 centimeters of suitably less than about 3.5 minutes, more suitably less than about 3 minutes, and most suitably less than about 2.5 minutes. As used herein, the Wicking Time value of an absorbent structure is meant to represent the time needed to transport a liquid a specified vertical distance away from a centralized liquid insult location. The Wicking Time value of a liquid to an elevation of 15 centimeters for an absorbent structure may be measured according to the test method described herein.

The absorbent structure of the present invention should have a density such that the absorbent structure exhibits the desired liquid transport properties described herein. The density of an absorbent structure generally determines the porosity, permeability, and capillary structure of the absorbent structure. If the density of the absorbent structure is too high, the capillaries of the absorbent structure will generally be too small such that the capillaries provide a relatively high capillary tension force but, because of the relatively small capillaries, the permeability of the absorbent structure will be relatively low. If the permeability of the absorbent structure is relatively low, the absorbent structure will generally only transport relatively small amounts of liquid so that the vertical liquid flux rate of the absorbent structure will be relatively low at, for example, each of about 5 centimeters and of about 15 centimeters of height from a source of liquid.

Conversely, if the density of the absorbent structure is too low, the permeability of the absorbent structure will be relatively high. However, the capillaries of the absorbent structure will generally be relatively large such that the capillaries provide a relatively low capillary tension force that results in the absorbent structure being generally unable to quickly transport liquid to relatively high elevations such as about 15 centimeters of height from a source of liquid. Thus, such an absorbent structure may exhibit a relatively high vertical liquid flux rate at a height, for example, of about 5 centimeters of height from a source of liquid but the liquid will move slower and slower, or stop altogether, the higher the front of the wicked liquid. Thus, the vertical liquid flux rate of such an absorbent structure will be relatively low at, for example, about 15 centimeters of height from a source of liquid.

Depending on the stability of the capillary structure of an absorbent structure, the density of the absorbent structure may change as a liquid enters into the capillary structure of the absorbent structure. Generally, the structural stability of the absorbent structure will depend on such factors as the stability, as measured, for example, by shape, curl, stiffness, or resiliency, of the fibers in the absorbent structure as well as the stability of the absorbent structure as a whole. Structural changes of the absorbent structure are even more likely if the absorbent structure is under a stress or pressure as, for example, when the absorbent structure is used in a diaper being worn by a human. Thus, it is desirable that the density of the absorbent structure does not substantially change when the absorbent structure absorbs a liquid or otherwise becomes wet or is under a stress or pressure and/or that the absorbent structure substantially recovers its density after the liquid or stress or pressure is removed from the absorbent structure. The stability of the density of an absorbent structure may be quantified, for example, by the difference in densities exhibited by the absorbent structure when different loads, such as each of loads of about 0.15 pound per square inch and about 0.3 pound per square inch, are applied to the absorbent structure. If the difference in the densities exhibited by the absorbent structure at the different loads is relatively small, the absorbent structure may be considered to be structurally stable. Another method of characterizing the structure of an absorbent structure is by measuring the void volume of the absorbent structure.

TEST PROCEDURES

Population Average Fiber Length

Approximately 50 grams of a sample in slurry form, with a consistency between 0 weight percent and 5 weight percent, is placed into a container provided by Valmet Automation, to be used in conjunction with a Kajaani FS-200 Fiber Analyzer. Using another plastic container, the sample is washed back and forth allowing half of the sample to wash down the drain and the other half to fall into the plastic beaker. The washing is continued in this manner until it visually appears to have 30–60 fibers per second during testing. The container is then inserted into the Kajaani FS-200 Fiber Analyzer. Fiber length results are calculated by the analyzer and reported in millimeters.

Fiber Coarseness

Exactly 0.50 grams of fiber, in slurry form with a consistency not greater than 5 weight percent, is placed into a 2000 ml glass beaker and diluted to 2000±5 ml. A magnetic stirring bar is inserted into the beaker, and the beaker is placed on a magnetic stirrer. The stirrer is turned on, with the aim of achieving a two inch vortex within the slurry. A pipet is inserted at an angle into the slurry, and 50 ml of the slurry is removed while moving the pipet from top to bottom of the slurry. The 50 ml of slurry is placed into a container provided by Valmet Automation, to be used in conjunction with a Kajaani FS-200 Fiber Analyzer. Another 50 ml of distilled water is pipeted into the container, to wash away any fibers that may have adhered to the inside of the pipet. The container is then inserted into the Kajaani FS-200 Fiber Analyzer. Coarseness results are calculated by the analyzer and reported in milligrams/100 meters.

Preparation of Wet-Laid Handsheet

A 17 inch by 17 inch standard handsheet having a basis weight of about 200 grams per square meter was prepared using a desired fiber sample by using a 16 inch by 16 inch cast bronze wet-laid handsheet former mold, available from Voith Corporation.

A British Disintegrator mixer, available from Testing Machines, Inc., was filled with about 2 liters of water at room temperature (about 23° C.) and about 37.3 grams of the fiber sample. The counter on the British Disintegrator was set to zero and the cover was placed on the British Disintegrator. The British Disintegrator was turned on until the counter runs to about 600. Alternatively, the British Disintegrator may be run for about 5 minutes. A bucket was filled with about 8 liters of distilled water. The contents of the British Disintegrator was then also poured into the bucket. All the leftover fiber was also rinsed into the bucket.

The handsheet former, having an about 12 inch deep chamber, was filled with tap water to about 5 inches below the top of the handsheet former chamber. The contents of the bucket were then poured into the handsheet former chamber. A dedicated stirrer was then used to mix the suspension in the handsheet former chamber. The stirrer was moved slowly up and down 6 times to cause small vortexes, but to avoid causing large vortexes, in the square pattern of the handsheet former. The stirrer was then removed and the suspension was drained through the forming screen of the handsheet former. The handsheet former was then opened and two layers of blotting paper were placed on the top of the handsheet. A roller, having the equivalent of about 2.3 pounds of pressure per linear inch, was moved back and forth once on each of the left side, the right side, and the center of the formed handsheet. The blotting paper, with the formed handsheet attached, was then lifted off the forming screen. The blotting paper was then placed on a table such that the formed handsheet faced upwards. An 18 inch by 18 inch, 4 mesh stainless steel screen was placed on top of the handsheet. The blotting paper, handsheet, and screen were then flipped so that the screen was on the bottom and the blotting paper was on top. The blotting paper was then peeled off of the handsheet, leaving the handsheet on the screen. The edges of the handsheet were fastened to the screen using binder clips. The handsheet, attached to the screen, was then placed in an oven and dried at about 105° C. for about an hour. The handsheet was left overnight to air-dry. The handsheet was then removed from the oven and removed from the screen. The handsheet was then ready for evaluation for liquid distribution properties.

Bulk and Dry Density of an Absorbent Structure

From a handsheet prepared according to the procedure described herein, a strip of sample handsheet material, having a width of about 2 inches and a length of about 15 inches, was obtained by using a textile saw available, for example from Eastman, Machine Corp., Buffalo, N.Y. The sample strip was cut at least about 1 inch away from the edge of the handsheet so as to avoid edge effects. The sample strip was marked in about 10 millimeter intervals using water-soluble ink.

To measure the bulk of the sample strip, a bulk meter accurate to at least about 0.01 millimeter, such as a bulk meter available from Mitutoyo Corporation, was used. An about one inch diameter platen was used to measure the bulk, with the platen being parallel to the base of the bulk meter. The bulk of the sample strip was measured in about 50 millimeter intervals along the length of the sample strip and then averaged. The average bulk of the sample strip was then used to calculate the dry density of the sample strip, using the weight and dimensions of the sample strip. The wet density of the sample strip may be similarly determined after the sample strip has evaluated for Liquid Flux values.

Wicking Time and Vertical Liquid Flux of an Absorbent Structure

From a handsheet prepared according to the procedure described herein, a strip of sample handsheet material, having a width of about 2 inches and a length of about 15 inches, was obtained by using a textile saw available, for example from Eastman, Machine Corp., Buffalo, N.Y. The sample strip was cut at least about 1 inch away from the edge of the handsheet so as to avoid edge effects.

The Vertical Wicking Flux rate setup consisted of a constant fluid height in a reservoir which is maintained using a vented flask. Both the reservoir and the vented flask were positioned onto a balance. A sample of the absorbent material was hung in a holder above the reservoir. The sample was raised and lowered in and out of the reservoir by manually adjusting a slide. The volume of fluid absorbed by the sample was measured and recorded through interfacing the balance to a personal computer. Sensors, imbedded into the sample at 0.5 cm, 5.5 cm, 10.5 cm, and 15.5 cm heights, were connected to a electrical relay box which is also integrated to the computer. These sensors were used to measure the time it took for the fluid front to reach each sensor. The sample holder was a plastic ruler with 4 pins positioned 0.5 cm, 5.5 cm, 10.5 cm, and 15.5 cm up from the base. The ruler hung from a manually operated slide into a plexiglass box to shield it from wind currents. There was a clamp at the top of the ruler to hold the sample and the sample was 2 inches by 10 inches. The holder containing the sample was suspended over the reservoir from the slide. When the sample was lowered and contacted the fluid reservoir a computer program initiated the recording of readings off the balance as well as timing of the sensors. The timers stopped when the sensors were contacted by fluid.

The computer program created a file containing the essential sample data, fluid pickup data, and the time to reach the sensors. This file was further analyzed and the results reported were: 1) time to reach each height, and 2) the rate or flux of fluid entering the sample at the moment the fluid front reached each of the recorded heights. The Vertical Liquid Flux value of the sample strip at a particular height was calculated by dividing the grams of liquid absorbed by the sample strip by each of: the basis weight, in grams per square meter, of the sample strip; the time, in minutes, needed by the liquid to reach the particular height; and the width, in inches, of the sample strip.

The fluid used was Baxter Blood Bank Saline. The use of saline aided in the conductivity within the wetted portion of the sample to the probes. Conditioning and testing of materials was carried out in an atmosphere with a temperature of 23±1° C. (73.4±1.8° F.) and relative humidity of 50±2 percent.

EXAMPLES

Example 1

A never dried, southern softwood kraft pulp (available from Kimberly-Clark Corporation under the designation CR54 southern softwood kraft pulp) was used as a cellulosic fiber sample. This cellulosic fiber sample was fractionated by using a classifier available from Testing Machines, Inc. under the designation Bauer-McNett classifier, according to the procedure described in TAPPI standard test method T233, incorporated herein in its entirety by reference. Various fractions of the cellulosic fiber sample were collected and evaluated for Fiber Length and Fiber Coarseness, according to the procedures described in the Test Methods section herein. Handsheets were then prepared, from the various fractions of the cellulosic fiber sample, and evaluated according to the procedures described in the Test Methods section herein. The results of these evaluations are summarized in Table 1. The unfractionated never dried, southern softwood kraft pulp is listed as the Control material. The 100 mesh and 200 mesh fractions, representing about 5.9 weight percent of the total original cellulosic fiber sample, were combined as a single mixture for the purposes of forming a handsheet. The fines were not collected and were not formed into a handsheet.

TABLE 1

| Screen Size | Population Average Fiber Length (mm) | Fiber Coarseness (mg/100 m) | Wicking Time to 15 cm (sec) | Wicking Flux at 15 cm (g/in min gsm) |
|---|---|---|---|---|
| Control | 0.70 | 25.6 | 215 | 18 |
| +14 mesh | 2.52 | 31.1 | 162 | 32 |
| +28 mesh | 2.46 | 26.0 | 179 | 28 |
| +48 mesh | 1.63 | 20.3 | 227 | 26 |
| +100 mesh | 0.86 | 16.6 | 433 | 11 |
| +200 mesh | 0.41 | 14.5 | — | — |
| −200 mesh | — | — | — | — |

Example 2

A never dried, southern softwood kraft pulp (available from Kimberly-Clark Corporation under the designation CR54 southern softwood kraft pulp) was used as a cellulosic fiber sample. This cellulosic fiber sample was fractionated by using a cleaner available from Alfa Laval Celleco Inc. under the designation Cleanpac 350 cleaner. The cleaner is a conically shaped vessel which utilizes fluid pressure energy to create rotational fluid motion. A dilute cellulosic fiber slurry is introduced tangentially near the top of the cleaner body through a feed connection. The tangential inlet causes a rapid rotation of the fiber slurry as well as a downward movement in the cone. The coarse fibers migrate to the walls of the cone, moving downward on the walls of the cleaner and move out at the bottom outlet. The free upward vortex created in the center of the cone carries the less coarse fibers through the top central outlet. The cleaner was used at various inlet consistencies and various pressure drops. The yield of the collected fractions was generally about 25 weight percent of the original cellulosic fiber sample. Various fractions of the cellulosic fiber sample were collected and evaluated for Fiber Length and Fiber Coarseness, according to the procedures described in the Test Methods section herein. Handsheets were then prepared, from the various fractions of the cellulosic fiber sample, and evaluated according to the procedures described in the Test Methods section herein. The results of these evaluations are summarized in Table 2. The unfractionated never dried, southern softwood kraft pulp is listed as the Control material.

TABLE 2

| Test # | Inlet Consistency (%) | Pressure Drop (psi) | Population Ave. Fiber Length (mm) | Fiber Coarseness (mg/100 m) | Wicking Time to 15 cm (sec) | Wicking Flux at 15 cm (g/in*min*gsm) |
| --- | --- | --- | --- | --- | --- | --- |
| Control | — | — | 0.73 | 27.2 | 307 | 0.0013 |
| 1 | 0.2 | 20 | 1.03 | 29.0 | 161 | 0.0026 |
| 2 | 0.2 | 40 | 1.09 | 32.3 | 177 | 0.0025 |
| 3 | 0.2 | 55 | 1.15 | 31.4 | 159 | 0.0025 |
| 4 | 0.45 | 20 | 1.01 | 29.9 | 175 | 0.0023 |
| 5 | 0.45 | 40 | 1.04 | 29.7 | 164 | 0.0025 |
| 6 | 0.45 | 55 | 0.97 | 31.5 | 161 | 0.0025 |
| 7 | 0.7 | 20 | 1.11 | 29.9 | 180 | 0.0022 |
| 8 | 0.7 | 40 | 1.04 | 30.1 | 199 | 0.0021 |
| 9 | 0.7 | 55 | 1.07 | 30.2 | 167 | 0.0023 |
| 10 | 0.83 | 20 | 0.90 | 30.1 | 195 | 0.0021 |
| 11 | 0.83 | 40 | 1.11 | 29.5 | 125 | 0.0025 |
| 12 | 0.83 | 50 | 1.12 | 31.4 | 140 | 0.0026 |

Example 3

A never dried, southern softwood kraft pulp (available from Kimberly-Clark Corporation under the designation CR54 southern softwood kraft pulp) was used as a cellulosic fiber sample. This cellulosic fiber sample was fractionated by using a screen available from Alfa Laval Celleco Inc. under the designation SPRAYDISC screen. A dilute cellulosic fiber slurry is sprayed against two rotating filter media discs at a pressure of between 15 to 35 pounds per square inch. The long fiber fraction is retained on the discs with the short fiber fraction passes through the discs. As the discs rotate at about 30 to about 60 revolutions per minute, the centrifugal force causes the retained fibers to move radically on the discs and discharge at the periphery. Cleaning showers using filtrate keep the discs clean. Both the long fiber fraction and short fines fiber fractions are discharged from the filter by gravity. The cellulosic fiber sample was fractionated using 3 stages of the screen in a series. The first stage used a filter media having a size of about 800 micrometers, a pressure of about 30 pounds per square inch, a disc speed of about 60 revolutions per second, and an inlet consistency of about 0.7 weight percent. The second stage used a filter media having a size of about 800 micrometers, a pressure of about 30 pounds per square inch, a disc speed of about 60 revolutions per second, and an inlet consistency of about 0.8 weight percent. The third stage used a filter media having a size of about 1000 micrometers, a pressure of about 15 pounds per square inch, a disc speed of about 60 revolutions per second, and an inlet consistency of about 0.9 weight percent. The third stage coarse fiber was taken through an additional thickening step for easier shipment. A bow screen with a 0.004 inch slot was used for thickening the fibers. The bow screen is a curved, sloping, stationary gravity screen. The bow stage used a pressure of about 5 pounds per square inch and an inlet consistency of about 1.2 weight percent. The total yield of the collected cellulosic fiber fractions was about 80 weight percent of the original cellulosic fiber sample. The various fractions of the cellulosic fiber sample were collected and evaluated for Fiber Length and Fiber Coarseness, according to the procedures described in the Test Methods section herein. Handsheets were then prepared, from the various fractions of the cellulosic fiber sample, and evaluated according to the procedures described in the Test Methods section herein. The results of these evaluations are summarized in Table 3.

TABLE 3

| | Population Average Fiber Length (mm) | Fiber Coarseness (mg/100 m) | Wicking Time to 15 cm (sec) | Wicking Flux at 15 cm (g/in*min*gsm) |
| --- | --- | --- | --- | --- |
| Feed | 0.76 | 21.4 | 318 | 0.0012 |
| 1st Stage | 1.17 | 23.6 | 174 | 0.0022 |
| 2nd Stage | 1.50 | 24.9 | 172 | 0.0025 |
| 3rd Stage/ Bow Screen | 1.91 | 28.9 | 130 | 0.0033 |

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. A disposable, absorbent product comprising:
   a liquid-permeable topsheet;
   a backsheet attached to the liquid-permeable topsheet; and
   an absorbent structure positioned between the liquid-permeable topsheet and the backsheet, the absorbent structure comprising
      fractionated cellulosic fibers exhibiting a fiber coarseness value greater than about 20 milligrams per 100 meters and a population average fiber length greater than about 0.9 millimeters,
   wherein the absorbent structure exhibits a vertical liquid flux rate value at a height of about 15 centimeters of at least about 0.002 grams of liquid per minute per square meter of absorbent structure per inch of cross-sectional width of absorbent structure.

2. The disposable, absorbent product of claim 1 wherein the fractionated cellulosic fibers are from a wood source.

3. The disposable, absorbent product of claim 1 wherein the fractionated cellulosic fibers exhibit a fiber coarseness value greater than about 22 milligrams per 100 meters.

4. The disposable, absorbent product of claim 1 wherein the fractionated cellulosic fibers exhibit a fiber coarseness value greater than about 24 milligrams per 100 meters.

5. The disposable, absorbent product of claim 1 wherein the fractionated cellulosic fibers exhibit a fiber coarseness value greater than about 26 milligrams per 100 meters.

6. The disposable, absorbent product of claim 1 wherein the fractionated cellulosic fibers exhibit a population average fiber length value greater than about 1.0 millimeters.

7. The disposable, absorbent product of claim 1 wherein the fractionated cellulosic fibers exhibit a population average fiber length value greater than about 1.1 millimeters.

8. The disposable absorbent product of claim 1 wherein the fractionated cellulosic fibers are wettable.

9. The disposable absorbent product of claim 1 wherein the fractionated cellulosic fibers comprise substantially individual fibers.

10. A process for making a disposable, absorbent product, the process comprising the steps of:

providing a first cellulosic fiber mixture;

fractionating the first cellulosic fiber mixture into a second cellulosic fiber mixture and a third cellulosic fiber mixture, wherein the second cellulosic fiber mixture exhibits a fiber coarseness value greater than about 20 milligrams per 100 meters and a population average fiber length value greater than about 0.9 millimeters;

forming a fibrous matrix from the second cellulosic fiber mixture;

incorporating the fibrous matrix into an absorbent structure, wherein the absorbent structure exhibits a vertical liquid flux rate value at a height of about 15 centimeters of at least about 0.002 grams of liquid per minute per gram per square meter of absorbent structure per inch of cross-sectional width of absorbent structure;

providing a liquid-permeable topsheet;

providing a backsheet;

positioning the absorbent structure so that the absorbent structure is between the liquid-permeable topsheet and the backsheet in the disposable, absorbent product; and attaching the liquid-permeable topsheet to the backsheet.

11. The process of claim 10 wherein the first cellulosic fiber mixture is from a wood source.

12. The process of claim 10 wherein the second cellulosic fiber mixture exhibits a fiber coarseness value greater than about 22 milligrams per 100 meters.

13. The process of claim 10 wherein the second cellulosic fiber mixture exhibits a fiber coarseness value greater than about 24 milligrams per 100 meters.

14. The process of claim 10 wherein the second cellulosic fiber mixture exhibits a fiber coarseness value greater than about 26 milligrams per 100 meters.

15. The process of claim 10 wherein the second cellulosic fiber mixture exhibits a population average fiber length value greater than about 1.0 millimeters.

16. The process of claim 10 wherein the second cellulosic fiber mixture exhibits a population average fiber length value greater than about 1.1 millimeters.

17. The process of claim 10 wherein the first cellulosic fiber mixture comprises wettable fibers.

18. The process of claim 10 wherein the second cellulosic fiber mixture comprises wettable fibers.

19. The process of claim 10 wherein the first cellulosic fiber mixture comprises substantially individual fibers.

* * * * *